United States Patent [19]

Shikano et al.

[11] Patent Number: 5,164,373

[45] Date of Patent: Nov. 17, 1992

[54] THERAPEUTIC AGENT FOR DIABETIC GANGRENE COMPRISING FACTOR XIII

[75] Inventors: Masahiko Shikano, Gifu; Satoshi Tanaka, Toride; Masao Ikdea; Hiroshi Nin, both of Yokohama, all of Japan

[73] Assignee: Hoechst Japan Limited, Tokyo, Japan

[21] Appl. No.: 656,472

[22] Filed: Feb. 15, 1991

[30] Foreign Application Priority Data

Feb. 20, 1990 [JP] Japan .................................. 2-37284

[51] Int. Cl.⁵ .................. A61K 35/16; A61K 37/02; A61K 37/48; A61K 35/50
[52] U.S. Cl. .................................. 514/21; 424/94.61; 424/94.63; 424/94.64; 424/94.65; 424/94.66; 514/2; 514/8; 514/12; 530/381
[58] Field of Search ............................ 514/2, 8, 21, 12; 530/381; 424/94.61, 94.63, 94.64, 94.65, 94.66

[56] References Cited

U.S. PATENT DOCUMENTS

| | | | |
|---|---|---|---|
| 3,904,751 | 9/1975 | Zwisler et al. | 530/381 |
| 3,931,399 | 1/1976 | Bohn et al. | 530/381 |
| 4,285,933 | 8/1981 | Fukushima et al. | 530/381 |
| 4,297,344 | 10/1981 | Schwinn et al. | 530/381 |
| 4,327,086 | 4/1982 | Fukushima et al. | 530/381 |
| 4,597,899 | 7/1986 | Falke | 514/21 |
| 4,909,251 | 3/1990 | Seelich | 514/2 |

FOREIGN PATENT DOCUMENTS

| | | | |
|---|---|---|---|
| 0011739 | 6/1980 | European Pat. Off. | 530/381 |
| 0037078 | 10/1981 | European Pat. Off. | 530/381 |

*Primary Examiner*—Howard E. Schain
*Attorney, Agent, or Firm*—Finnegan, Henderson, Farabow, Garrett and Dunner

[57] ABSTRACT

An agent for the therapy of diabetic gangrene is described containing blood coagulation factor XIII as the active ingredient.

10 Claims, No Drawings

THERAPEUTIC AGENT FOR DIABETIC GANGRENE COMPRISING FACTOR XIII

BACKGROUND OF THE INVENTION

1. Field of the Invention

This invention relates to therapeutic agents for diabetic gangrene.

2. Description of the Prior Art

Diabetic gangrene usually appears superveniently in patients of poorly controllable advanced diabetes and often occurs in endings of the extremities such as fingers and toes. Onset frequency of the disease has been increasing year by year.

Although it is believed that onset of the disease is triggered by defective blood flow due to arteriosclerotic lesion or is a vascular disease at peripheral smaller blood vessels, there is no established concept at present.

For treating diabetic gangrene, conservative treatment and surgical treatment have heretofore been applied. Trials of the conservative treatment include physical treatment such as bathing of the affected parts or kinesiotherapy and local treatment by application of various ointment such as antibiotics, local blood anticoagulant, fibrinolysin or insulin. In pharmacotherapy there are mainly employed peripheral vasodilator such as prostaglandin formulations. These therapeutics, however, have not been established as reliable.

In cases where the conservative treatment is ineffective, surgical treatment such as bypassing, sympathetic ganglionectomy in limbus, vascular transplantation and amputation is applied but prognosis after amputation of the lower extremities is very bad.

DETAILED DESCRIPTION OF THE INVENTION

It is an object of the invention to provide therapeutic agents for diabetic gangrene that are highly effective at earlier stages of the therapy.

This invention relates to therapeutic agents for diabetic gangrene which contain human blood coagulation factor XIII (hereinafter referred to as factor XIII) as the principal ingredient.

Factor XIII preparations have been used mainly to treat would healing disturbances. We have now found that factor XIII exerts an action to ameliorate diabetic gangrene. This finding has led us to accomplishment of the invention.

Factor XIII had also been called fibrin-stabilizing factor, fibrinase or plasma transglutaminase, the existence of which was suggested by Robbins in 1944. After studies by Laki and Lorand, et al., factor XIII was adopted as its official name at the Congress of the International Society of Thrombosis and Haemostasis in 1963. It is commonly seen in plasma, placenta, etc. In acts as a transaminase which is activated by thrombin and $Ca^{24}$ and forms cross-links between fibrin molecules. These cross-links grow into a strong fibrin network that is stable against mechanical and physical attacks. Besides this fibrin-stabilizing effect, it has also been demonstrated taht factor XIII plays an important role in would healing process by forming a cross-link between fibrin and fibronectin and also promoting fibroblast proliferation and epidermis formation.

Factor XIII preparations have already been in wide use as a therapeutic agent for wound healing disturbances, etc. Judging from domestic and overseas experiences of their use in patients exceeding 10,000, they are totally free from side effects and toxicity at a usual dose of about 20-50 units per Kg bodyweight.

Effectiveness of factor XIII in diabetic gangrene will be described in detail below with reference to clinical trial.

SUBJECTS

Seven patients of diabetic gangrene at ages from 49 to 71 (5 males and 2 females, all suffering from insulin-independent diabetes) who had been hospitalized from January to November, 1989 and treated in the department of internal medicine of a hospital.

RESULT

All of the 7 patients had a factor XIII level of 70% or below of the normal one. Administration of a factor XIII preparation of 1500U over a period of 5 day resulted in normalization of the factor XIII level in all cases. In 2 or 3 days from the start of the administration apparent initial degeneration of the gangrene was observed thereby demonstrating a remarkable effect as compared with conventional treatments.

PROCESS FOR PRODUCING FACTOR XIII CONCENTRATE

Factor XIII preparations are manufactured from human placenta or plasma by well-known methods. An example of the manufacturing methods using human placenta as raw material is as follows:

Freeze placentae and break them into fine pieces. Add an NaCl solution to the fine pieces of placentae, stir, and centrifuge to collect supernatant I. After ascertaining by enzyme immunoassay that this supernatant I is free from HBs antigen, add a Rivanol solution to it and collect precipitate II that contains factor XIII. After washing the precipitate, add an NaCl solution containing EDTA to it and stir. Remove undissolved substances (precipitate III) and obtain supernatant III. Then add an N-cetyl-pyridinium chloride solution to supernatant III to precipitate contaminating proteins and muco-polysaccharides. Add a Rivanol solution to the supernatant IV so obtained, and generate precipitate V that contains factor XIII. Add an NaCl solution containing EDTA to this precipitate V, stir, and remove undissolved substances (precipitate VI) to obtain supernatant VI. Add ammonium sulfate to supernatant VI to generate precipitate VII that contains factor XIII. Add an EDTA solution to precipitate VII and dialyze against a Tris-HCl buffer containing EDTA and sodium azide. After adjusting pH, remove precipitate VIII and have supernatant VIII undergo gel filtration to collect active fractions. Add ammonium sulfate to the fractions and generate precipitate IX containing factor XIII. Dissolve this precipitate IX in a Tris-HCl buffer containing EDTA, dialyze against the same buffer, and adjust pH to collect a precipitate that contains factor XIII in the form of euglobulin. Dissolve the euglobulin precipitate in an NaCl solution containing EDTA, and add aminoacetic acid and sucrose. Then add ammonium sulfate to generate precipitate X containing factor XIII, and dissolve this precipitate X in an NaCl solution containing EDTA, and dialyze against the same solution. Adjust the titer of factor XIII using an NaCl solution containing glucose and human serum albumin. Have this solution undergo sterile filtration, dispense into glass vials, and lyophilize.

In addition to the above-mentioned fractionation method, factor XIII can also be manufactured by the use of genetic engineering. Factor XIII preparations in accordance with this invention include all the factor xIII preparations manufactured by any possible method, including fractionation methods and genetic engineering methods. Since factor XIII preparations manufactured by fractionation methods ma possibly contain hepatitis virus, AIDS virus, etc., it is desired to inactivate these viruses by heat treatment or some other means. The heat treatment is performed as follows: Dissolve the precipitate containing factor XIII in the form of euglobulin in an NaCl solution containing EDTA, and allow the solution to stand at approximately 60° C. for 10 hours or so. Amino acids, e.g., glycine, saccharide, etc. can be used as stabilizers in the heat treatment.

The lyophilized factor XIII preparation can directly be used as an injection by dissolving it in distilled water for injection (JP), etc. just before use. Concentration of factor XIII in the solution for injection should be about 250 units/4 ml. The injection can be given either intravenously or intramuscularly. No problem of the factor XIII solution has been reported in compatibility with other agents. It is generally cautioned, however, that administration by injection of factor XIII mixed with other agents should be avoided.

Most desirably, factor XIII should be administered by injection, but possible dosage forms include parenteral ones such as micro-capsules and implants, oral ones such as liquids, tablets and capsules, and external ones such as ointments and suppositories.

DOSAGE AND TREATMENT PERIOD

The daily dosage for diabetic gangrene patients is approximately 1500 units.

Administration should be continued until degeneration or cure of the gangrene is observed, i.e., for 5 days in usual cases. In cases where recurrence or occurrence at other sites is observed, the administration may be restarted at any time.

EXAMPLE

Factor XIII, dispensed into vials with a potency adjusted to 250 units each and lyophilized, was dissolved in 4 ml of distilled water for injection (JP) to make a factor XIII injection.

What is claimed is:

1. A method of treatment of diabetic gangrene comprising administering human blood coagulation factor XIII as an active ingredient.

2. A method of treatment of diabetic gangrene as claimed in claim 1 comprising a route of administration selected from the group consisting of injection, parenteral administration, microcapsules, implants, liquids, tablets, capsules, ointments and suppositories.

3. A method of treating diabetic gangrene as claimed in claim 1 comprising administration of approximately 1,500 units of human blood coagulation factor XIII for two to five days.

4. A method of treating diabetic gangrene as claimed in claim 1 comprising administration of human blood coagulation factor XIII for about five days.

5. A method of treating diabetic gangrene as claimed in claim 1 wherein the factor XIII is obtained from human placenta or plasma.

6. A method of treating diabetic gangrene as claimed in claim 1 wherein the factor XIII is obtained by manufacture using genetic engineering.

7. A method of treatment of diabetic gangrene as claimed in claim 1 wherein factor XIII is obtained by fractionation methods.

8. A method of treatment of diabetic gangrene as claimed in claim 7 wherein the factor XIII is treated before administration to remove any virus.

9. A method of treatment of diabetic gangrene as claimed in claim 8 wherein the factor XIII is treated by the steps of:
a) dissolving the precipitate factor containing factor XIII in the form of euglobulin in an NaCl solution containing EDTA, and
b) allowing the solution to stand at approximately 60° C. for ten hours.

10. A method of treating diabetic gangrene as claimed in claim 9, wherein amino acids are used as stabiliziers in the heat treatment.

* * * * *